(12) United States Patent
Chiang et al.

(10) Patent No.: US 7,722,748 B2
(45) Date of Patent: May 25, 2010

(54) APPARATUS FOR MEASURING ELECTROCHEMICAL CORROSION

(75) Inventors: Kuang-Tsan Kenneth Chiang, Helotes, TX (US); Lietai Yang, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 422 days.

(21) Appl. No.: 11/682,571

(22) Filed: Mar. 6, 2007

(65) Prior Publication Data

US 2008/0217172 A1 Sep. 11, 2008

(51) Int. Cl.
*G01N 27/30* (2006.01)
(52) U.S. Cl. ...................................... 204/404; 204/400
(58) Field of Classification Search .................. 204/400, 204/404; 205/775, 775.5
See application file for complete search history.

(56) References Cited

U.S. PATENT DOCUMENTS

| | | | |
|---|---|---|---|
| 3,772,178 A | | 11/1973 | Wilson |
| 4,155,354 A | | 5/1979 | Rasmussen |
| 5,019,184 A | * | 5/1991 | Crum et al. ................. 148/676 |
| 5,455,072 A | | 10/1995 | Bension et al. |
| 5,580,431 A | * | 12/1996 | Isaacs et al. ................. 205/656 |
| 5,695,832 A | | 12/1997 | Hirano et al. |
| 5,712,000 A | | 1/1998 | Wei et al. |
| 5,712,559 A | | 1/1998 | Moore et al. |
| 5,780,119 A | | 7/1998 | Dearnaley et al. |
| 5,793,042 A | | 8/1998 | Quick |
| 5,840,427 A | | 11/1998 | Babu et al. |
| 5,880,552 A | | 3/1999 | McGill et al. |
| 5,965,217 A | | 10/1999 | Sugiyama et al. |
| 6,320,295 B1 | | 11/2001 | McGill et al. |
| 6,332,363 B1 | | 12/2001 | Molloy et al. |
| 6,531,182 B2 | | 3/2003 | Veerasamy et al. |
| 6,592,519 B1 | | 7/2003 | Martinez |
| 6,607,642 B1 | | 8/2003 | Kiesele et al. |
| 6,683,463 B2 | | 1/2004 | Yang et al. |
| 6,987,396 B2 | | 1/2006 | Yang et al. |
| 7,034,553 B2 | | 4/2006 | Gilboe |
| 7,180,309 B1 | | 2/2007 | Yang |
| 7,245,132 B1 | | 7/2007 | Poirier et al. |
| 7,282,928 B1 | | 10/2007 | Hladky et al. |
| 7,309,414 B2 | | 12/2007 | Yang |
| 7,368,050 B2 | | 5/2008 | Jovancicevic et al. |

(Continued)

FOREIGN PATENT DOCUMENTS

WO 02077615 10/2002

OTHER PUBLICATIONS

Yang, Lietai. "Measurement of Corrosion in Saturated Solutions Under Salt Deposits Using Coupled Multielectrode Array Sensors." Corrosion, Paper No. 03426. 2003.*

(Continued)

*Primary Examiner*—Alex Noguerola
(74) *Attorney, Agent, or Firm*—Grossman Tucker et al (57) ABSTRACT

Disclosed herein is an electrochemical corrosion sensor. The sensor may include an array of electrodes wherein each electrode may include a diamond like carbon coating disposed on at least a portion of the electrodes. The coating thickness may be at least about 1 micron. The electrodes may therefore provide relatively more accurate determination of electrode corrosion rates that may be more consistent with coupon type gravimetric testing.

18 Claims, 7 Drawing Sheets

U.S. PATENT DOCUMENTS

2003/0199741 A1   10/2003   Martinez
2005/0246002 A1   11/2005   Martinez
2005/0274628 A1   12/2005   Yang

OTHER PUBLICATIONS

Chinese Patent Office English language machine translation of CN 1548584 A, patent published Nov. 24, 2004.*

Derwent English language abstract of CN 1548584 A, patent published Nov. 24, 2004.*

Lietai Yang, et al. Southwest Research Institute. IR&D. "Development of a Multielectrode Array Sensor for Monitoring Localized Corrosion, 20-9209". Inclusive Dates: Aug. 1, 2000-Current. htpp://www.swri.org/3pubs/IRD2001/20-9209.htm. Internet printout dated Jan. 31, 2007. 2pgs.

Southwest Research Institute® "Ion Surface Engineering". www.surfaceengineering.swri.com. Published in Apr. 2004. Surface Engineering Section, Mechanical and Materials Engineering Division, Southwest Research Institute, 6220 Culebra Road, P.O. Drawer 28510, San Antonio, Texas 78228-0510. Tel: (210) 522-6588. Fax: (210) 522-6220. 12pgs.

Anderko, et al, "Validation of Localised Corrosion Model Using Real Time Corrosion Monitoring in a Chemical Plant," Corrosion Engineering, Science and Technology, 2005, vol. 40, No. 1 (10 pages).

Chiang, et al., "Monitoring Corrosion Behavior of a Cu—Cr—Nb Alloy by Multielectrode Sensors," Corrosion NACExpo 2006, 61st Annual Conference and Exposition, Paper No. 06676 (19 pages).

Wall, "Applications of Multi-electrode Techniques to Aqueous and Atmospheric Corrosion Testing," Corrosion NACExpo 2006, 61st Annual Conference and Exposition, Paper No. 06672 (10 pages).

Sridhar, "Coupled Multielectrode Array Systems and Sensors for Real-Time Corrosion Monitoring—A Review," Corrosion NACExpo 2006, 61st Annual Conference and Exposition, Paper No. 06681 (46 pages).

Yang, et al., "Corrosion Behavior of Alloy 22 in Concentrated Nitrate and Chloride Salt Environments at Elevated Temperatures," NACE International Corrosion Conference and Expo 2007, paper No. 07580 (25 pages).

International Search Report and Written Opinion dated Jun. 30, 2008 issued in related International Patent Application No. 11682571 (9 pages).

Yang, L., et al., "Corrosion Behavior of Allow 22 in Concentrated Nitrate and Chloride Salt Environments at Elevated Temperatures," Corrosion 2007 Conference & Expo, 2007, Paper 07580, pp. 07580/1-07580/19, NACE International, U.S.A.

Wall, F.D., "Applications of Multi-Electrode Techniques to Aqueous and Atmospheric Corrosion Testing," Corrosion 2006, Paper 06672, pp. 06672/1-06672/10, NACE International, U.S.A.

Chiang, K.T., et al., "Monitoring Corrosion Behavior of a Cu—Cr—Nb Allow by Multielectrode Sensors," Corrosion 2006, Paper 06676, pp. 06676/1-06676/19, NACE International, U.S.A.

Yang, L., "Coupled Multielectrode Array Systems and Sensors for Real-Time Corrosion Monitoring—A Review," Corrosion 2006, Paper 06681, pp. 06681/1-06681/45, NACE International, U.S.A.

Anderko, A., "Validation of Localised Corrosion Model Using Real Time Corrosion Monitoring in a Chemical Plant," Corrosion Engineering, Science and Technology, 2005, 40(1):33-42, Maney, U.S.A.

* cited by examiner

APPARATUS FOR MEASURING ELECTROCHEMICAL CORROSION

FIELD

This disclosure relates to a corrosion resistant coating and in particular a corrosion resistant coating for use in combination with an array sensor for electrochemical corrosion monitoring.

BACKGROUND

Corrosion may generally be understood as a deterioration of one or more essential properties of a material, such as physical or mechanical properties. Corrosion may be caused by various environmental factors such as reaction with oxidation, hydrolysis, and attack by acids or bases, etc. Corrosion may also be localized in one area, while the remaining area of the component remains relatively unaffected, causing phenomena such as pitting. Such localized corrosion may lead to premature failure of a given material in the component, making it desirable to assess localized corrosion of the material using both real-time and offline measurement systems.

However, just as various engineering components are exposed to corrosive environments, the measurement systems, and in particular the sensors employed in such systems, are also exposed to the corrosive environments. Due to this exposure, crevices may form in the sensors between the electrode and the sensor housing materials. Such crevices may cause changes in the size of the exposed surfaces of the electrodes and affect the corrosion rate calculations, employing Faraday's Law, as applied to the electrochemical kinetics that may be used in corrosion monitoring.

SUMMARY

An aspect of the present disclosure relates to an electrochemical sensor for a corrosive environment. The sensor may include a plurality of electrodes including a diamond like coating on at least a portion of the electrodes. The coating may have a thickness of greater than 10 nanometers. The electrodes may also include an exposed surface area ($SA_1$), without the coating. The exposed surface area may remain substantially constant after exposure to a corrosive environment.

Another aspect of the present disclosure relates to a method of producing an electrochemical sensor capable of corrosion monitoring. The method may include depositing a diamond like carbon coating on at least a portion of an electrode, wherein the coating has a thickness of greater than 10 nanometers. The electrode may have an exposed surface area ($SA_1$), which may remain substantially constant after exposure to a corrosive environment.

BRIEF DESCRIPTION OF DRAWINGS

The detailed description below may be better understood with reference to the accompanying figures which are provided for illustrative purposes and are not to be considered as limiting any aspect of the invention.

DETAILED DESCRIPTION

The present invention relates to a corrosion resistant coating and in particular to a corrosion resistant coating that may be used in combination with a sensor for electrochemical corrosion monitoring. Such sensor may be suitable for use at elevated temperatures (e.g. at or above about 50° C.) in a corrosive environment. A corrosive environment may be understood herein as an environment wherein the pH is greater or lower than 7.0, and which may include one or more chemical compounds that may influence corrosions, such as an inorganic salt.

Figure 1:
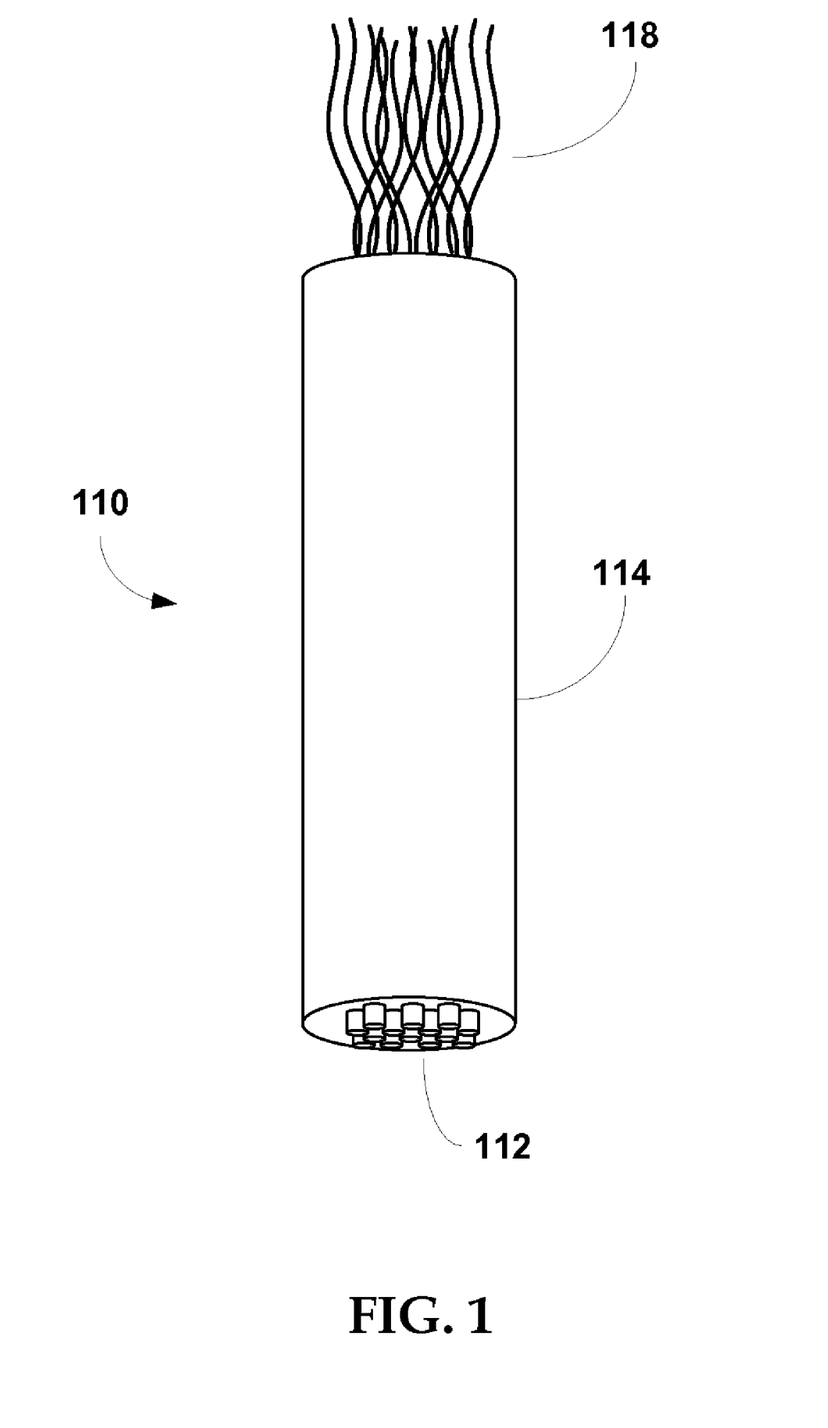
FIG. 1 is a perspective view of an exemplary electrochemical corrosion sensor.

The sensor may include one or more electrodes. When more than one electrode is present, the electrodes may be coupled in an array. An exemplary coupled multielectrode array sensor is illustrated in FIG. 1. As can be seen in the figure, the sensor 110 may include a number of electrodes 112 at least partially surrounded by a housing 114, wherein a portion of the electrodes 112 are exposed. In addition, each electrode 112 may be attached to an electrical connection 118, which may provide communication between the electrodes and a monitoring system (not illustrated).

An electrode may be understood as a conductive material, such as a wire. The electrode may have a length along a longitudinal axis and a cross-section generally perpendicular to the longitudinal axis. An exemplary electrode may be formed out of a material that exhibits similar corrosion characteristics as the component material to be modeled and therefore may be formed out of a material that is similar to the component to be modeled. For example, the electrode materials may include various metal alloys, which may include various transition metals such as nickel, iron, chromium, molybdenum, manganese, tungsten, cobalt, vanadium, titanium, copper, zinc, etc. In addition, the metal alloys may also include various metalloids such as carbon, phosphorus, sulfur, silicon, boron, aluminum, etc. Exemplary metal alloys may include nickel based alloys, which may include at least approximately 45 atomic percent (at %) nickel, such as in the range of 45 to 99 at % including all values and increments therein, wherein no other element is present at an at % greater than 30, such as in the range of 30 to 1%, including all values and increments therein.

Such nickel based alloys may also include chromium present in the range of about 10 to 30 at %, molybdenum present in the range of about 10 to 30 at % and W present in the range of about 1 to 10 at %. Optionally, the alloys may also include iron present in the range of about 0 to 10 at %, cobalt present in the range of about 0 to 5 at %, manganese present in the range of about 0 to 2 at %, vanadium present in the range of about 0 to 2 at %, as well as carbon present in the range of about 0 to 0.5 at %, phosphorous present in the range of about 0 to 0.5 at %, sulfur present in the range of about 0 to 0.1 at %, or silicon present in the range of about 0 to 0.1 at %. It may be appreciated that the ranges discussed above may all include values and increments within the levels specified. Furthermore, exemplary alloy compositions may include ($Ni_{59}Cr_{22}Mo_{13}Fe_3W_3$, $Ni_{60}Cr_{21}Mo_{12}W_3$,) ($Ni_{57}Cr_{14.5-16.5}Mo_{15-17}W_{3-4.5}C_{0.01}Co_{2.5}Fe_{4-7}Mn_1$—$P_{0.025}S_{0.01}Si_{0.08}V_{0.35}$,) ($Ni_{60}Cr_{20.5}Mo_{12-15}W_{2-4}$ $C_{0.015}Co_{2.5}Fe_{2-3}Mn_{0.5}P_{0.02}$—$S_{0.02}Si_{0.08}V_{0.35}$,) ($Ni_{56}Cr_{22}$—$Mo_{13}W_3C_{0.01}Co_{2.5}Fe_3Mn_{0.5}Si_{0.08}V_{0.35}$,) ($Ni_{57}Cr_{21.2}Mo_{13.5}W_3C_{0.07}$—$Co_{1.2}Fe_4Mn_{0.2}P_{0.01}Si_{0.04}V_{0.17}$,) ($Ni_{56}Cr_{22}Mo_{13}W_3C_{0.01}Co_{2.5}Fe_3Mn_{0.5}Si_{0.08}V_{0.35}$.) Note that the alloys may contain about 5 at % or less of various impurities, which may be present in trace amounts. In one exemplary embodiment, the alloy may be what is termed "Alloy 22." The electrical resistivity of the electrode may be in the range of $1\times10^{-4}$ to $2\times10^{-4}$ ohm, including all values and increments therein.

The electrodes may be coated with a corrosion resistant material. Exemplary corrosion resistant materials may include diamond like carbon coatings. Diamond like carbon (DLC) material may be understood as an amorphous carbon material or a hydrogenated amorphous carbon material that may be composed of a mixture of "sp$^2$" and "sp$^3$" bonded carbon. DLC coatings herein may also be understood to include those coatings that provide a Vickers Hardness (Hv) of greater than about 3000. For example, the DLC coatings herein may include coatings with a Hv that falls in the range of 3000-12000, including all values and increments therein.

Accordingly, DLC materials may include at least 50% carbon. In addition, the diamond like carbon material may be doped with various other materials, including metalloids or metals. The diamond like carbon coating may be deposited on the electrode surface via a number of deposition techniques, such as ion beam deposition. This may include direct and assisted techniques, pulsed laser deposition, plasma assisted chemical vapor deposition, or sputtering.

Figure 2:
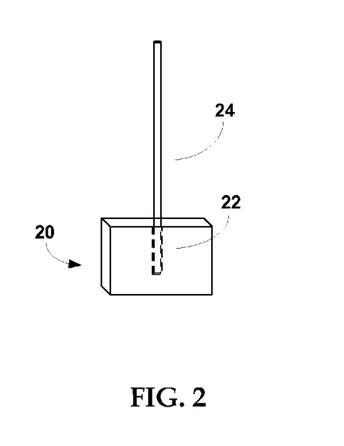
FIG. 2 is a perspective view of an electrode, as contemplated herein, positioned within a specimen holder.
Figure 3:
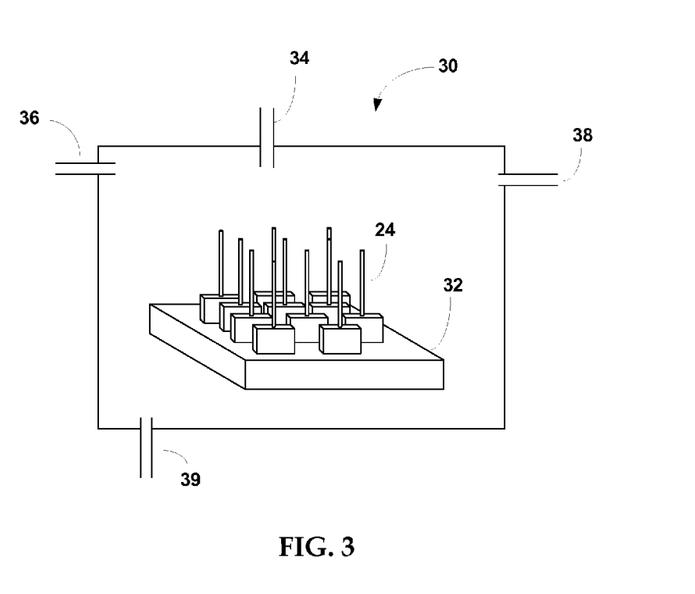
FIG. 3 is an illustration of an exemplary vacuum chamber.

In an exemplary embodiment, the electrodes may be placed onto specimen holders as illustrated in FIG. 2. The specimen holders 20 may include one or more pre-drilled holes 22 to retain the distal end of the electrode 24. The electrodes 24 may then be inserted into a vacuum chamber 30, as illustrated in FIG. 3 and placed onto a work table 32 in the chamber 30. The chamber may include a first gas inlet 34, a second gas inlet 36, an optional third gas inlet 38 and a vacuum port 39. Once placed into the chamber, the chamber may be sealed in a sufficient manner to draw a vacuum on the chamber. The chamber may be pumped down to a vacuum pressure of below $1\times10^{-3}$ Torr or to $1\times10^{-11}$ Torr, including all values and increments therein, such as $1\times10^{-5}$ Torr.

Ions may bombard the surface of the electrodes at a flow rate of 20 to 60 standard cubic centimeters per minute (sccm), including all increments and values therein, to clean the electrode surfaces. Cleaning may occur for a few seconds to a few hours, such as 10 seconds to 24 hours, including all values and increments therein, such as 1 hour. Exemplary ions utilized in cleaning may include those provided by argon, nitrogen or other relatively inert gasses. The ions may be fed through the first gas inlet 34.

An optional intermediate or bond layer may then be deposited which may include a non-metallic compound which may provide a bond layer in the form of a film which may improve the adhesion between the electrode and diamond like carbon material. For example, the bond layer may ultimately include silicon or a silicon compound. Various precursors or source gasses may be used, such as silane gas ($SiH_4$), disilane gas, etc. The precursor may be fed into the vacuum chamber at a flow rate in the range of 10 to 50 sccm, including all values and increments therein, such as 25 sccm. The silicon precursor may be supplied through the optional third gas inlet 38. Deposition may be completed in a few seconds to a few hours, including all values and increments therein, such as 30 seconds to 2 hours. The bond layer so formed may therefore include a layer of hydrogenated silicon (Si:H) and/or a hydrogenated silicon carbide ($Si_xC$:H).

The DLC compounds may then be applied to selected locations on the electrode using various hydrocarbon precursors. Hydrocarbon precursors may include gasses which contain carbon and hydrogen atoms. Such gasses may include $C_2$-$C_4$ alkenes, alkynes, $C_3$-$C_6$ cycloalkanes and/or aromatic hydrocarbons. These gasses may therefore include ethylene, propylene, butylene and 1,3-butadiene, acetylene, 1-propyne, cyclopropane, cyclohexane, benzene, styrene, toluene and xylene. In addition, methane and other alkanes may be used as well. The source gas may flow through the second gas inlet 36 in vacuum chamber at a flow rate of 10 to 100 sccm, including all values and increments therein, such as 60 sccm.

The coating process may be repeated one or more times to obtain a desired coating thickness. The DLC may therefore be present at a thickness of equal to or greater than about 10 nanometers (nm). Such thickness may also be in the range of about 10 nanometers to about 50 μm, including all values and increments therein. Ultimately, the coating may include one or more layers of DLC and, optionally, one or more bond layers. The various layers may be formed by varying or alternating the precursors fed through the vacuum chamber.

As noted, the coating process may be manipulated such that the diamond like carbon coating is applied to only portions of the electrode. In such a manner, the specimen holder described above may include a mask or other device to prevent the coating of an exposed surface area which may then provide a contact surface of the electrode for corrosion measurements. The exposed surface area ($SA_1$) may be located on an end or tip of the electrode such that the cross-sectional surface at the tip may be exposed and the diamond like carbon coating is then provided along at least a portion of the longitudinal (side) surfaces of the electrode. It may then be appreciated that when such electrode is positioned within a corrosive environment, for a time period suitable for electrochemical corrosion testing (e.g., greater than about 10 hours) only the surface area ($SA_1$) of the electrode is exposed to the environment. The longitudinal surfaces remain unexposed and intact due to the diamond like carbon coating.

Electrical contacts or connections may then be applied to the contact surface of the electrode. It may therefore be appreciated that in an exemplary embodiment, the exposed contact surface of the electrode may be provided on the opposite end of the electrode from the exposed surface area ($SA_1$) of the electrode while the sides of the electrode may be isolated from the corrosive environment.

It should be appreciated at this juncture, that the diamond like carbon coating provided along at least a portion of the longitudinal sides of the electrode may prevent the coated portions of the electrode from corroding in corrosive environments. Accordingly, corrosion may be substantially confined to only the exposed surface area ($SA_1$) at the tip of the electrode. In such a manner, the exposed surface area of the electrode, after exposure to a corrosive environment ($SA_2$), may remain relatively constant and may be only slightly greater than the exposed surface area ($SA_1$) prior to exposure to a corrosive environment. Such relatively constant surface area exposure may be such that it will ensure that the calculated localized corrosion rates (via, e.g., Faraday's Law noted above) will be relatively consistent and provide that such calculated corrosion rates will be consistent from actual determination of corrosion rates from comparative coupon testing (which measures actual weight loss). See, e.g., *Handbook On Corrosion Testing And Evaluation*, W. H. Ailor, Editor, J. Wiley (1971).

The relationship between the surface area prior to and after exposure may therefore be defined as follows:

$$(SA_2) \leq (1.05) \cdot (SA_1).$$

Thus, the surface area ($SA_2$) after exposure of the electrode to a corrosive environment may be no more than about five percent greater than the surface area ($SA_1$) of the electrode prior to the corrosive environment. In addition, ($SA_2$) may be less than five percent greater than ($SA_1$), including all values and increments between, e.g. 0.1% and 5.0 %. As therefore alluded to above, by maintaining such a relatively constant exposed surface area, the application of various calculations to determine the corrosion rate of a given substance may remain relatively accurate over a given time period of exposure to a given corrosive environment.

Figure 4:
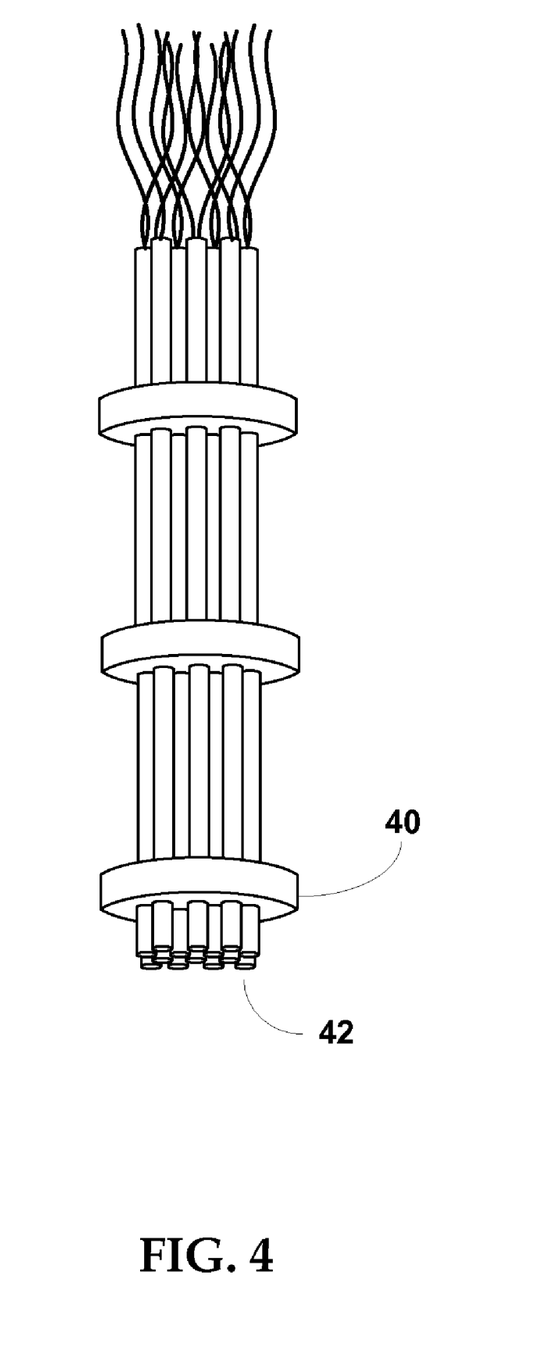
FIG. 4 is a perspective view of a number of electrodes positioned within housing spacers.
Figure 4A:
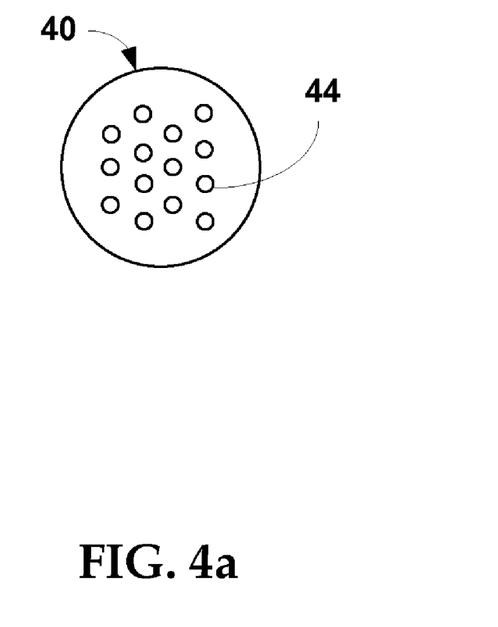
FIG. 4a is a top view of an exemplary spacer.

Turning back to the sensor assembly, the electrodes may also be mounted within the housing as generally illustrated in FIG. 1. The housing may be of a unitary piece, having a plurality of openings defined therein to accommodate the electrodes, or the housing may be formed from a number of pieces that are assembled together. In an exemplary embodiment, the electrodes 42 may be inserted into one or more holes 44, or openings defined in spacers 40 illustrated in FIGS. 4 and 4a. This assembly of electrodes and spacers may then be inserted into a hollow tube an affixed therein.

The spacers and tube may include materials that are capable of maintaining the spacing of the electrodes at elevated temperatures, such as greater than or equal to about 50° C. in a corrosive environment (pH greater than or less than 7.0), which conditions herein may be understood as a service temperature. Accordingly, the materials may have a service temperature in the range of about 50° C. to 300° C., including all ranges and increments therein. In addition, the materials may provide insulation between the electrodes and may exhibit an electrical volume resistivity in the range of about $1\times10^{11}$ to $1\times10^{18}$ ohm-cm, including all values and ranges therein. Such materials may include, for example, polytetrafluoroethylene, polyvinylidene fluoride, and other fluorinated polymers (polymers containing C—F bonds), ultra high molecular weight polyethylene, epoxy, etc. The spacer and tube materials may be the same or different materials.

The electrodes may be mounted into the sensor housing with a material that may similarly withstand the service temperature requirements noted above and maintain the electrodes in the sensor in a desired position. For example, one may employ a thermoset polymer resin, which may be understood as a polymer formed with crosslinking such that it will no longer indicate a defined melting point (Tm). The thermoset may also surround at least a portion or the entirety of the electrode and form an interface between the electrode and the housing. The thermoset resin may include resins such as epoxy resins formed from the diglycidyl ether of bisphenol A (DGEBPA), which may be cured with amine or acid compounds. In an exemplary embodiment, the electrodes may be mounted flush to the end of the housing and/or a spacer, such that only the cross-sectional ends of the electrodes are exposed.

The impedance of the electrodes may be measured via electrochemical impedance spectroscopy, which may be understood as applying an AC potential over a range of frequencies to an electrochemical cell and measuring the current through the cell. For example, to form the electrochemical cell, the electrodes may be inserted into an acidic solution of 0.1M of NaCl having a temperature of about 25° C. The electrodes may exhibit an impedance of at least about $1\times10^6$ ohm at a frequency of less than or equal to about 1 Hz.

In operation, the sensor may be used to model or monitor a material of interest by placing the electrodes (formed from such material) in the same or a similar environment for which the material may be exposed. For example, the sensor herein may be employed to specifically monitor corrosion of what is known as Alloy 22 which is also identified as UNS N06022 Nickel Superalloy. Such alloy contains the following elements in the indicated weight percents: C (0.07); Co (1.2); Cr (21.2); Fe (4); Mn (0.2); Mo (13.5); Ni (57); P (0.01); Si (0.04); V (0.17) and W (3). In addition, such alloy is employed as a nuclear waste packaging material in the above referenced corrosive environments thereby underscoring the importance of accurately monitoring its corrosion resistance.

In addition, those materials herein that may also be monitored for corrosion may include materials employed in bridges, process vessels, process pipelines, or even packaging material. In one particular embodiment, the electrode of a given material may be exposed to elevated temperatures above or about 70° C. In addition, the material may be exposed to one or more corrosive materials, such as water, oxygen, acids, bases, etc. In a particular embodiment, the material may be exposed to salts or acidic salt mixtures such as NaCl, $NaNO_3$, $KNO_3$, HCl, $HNO_3$ or combinations thereof.

EXAMPLES

The following examples are provided for the purposes of illustration and are not meant to limit the scope of the description or claims appended herein.

Example 1

Figure 5:
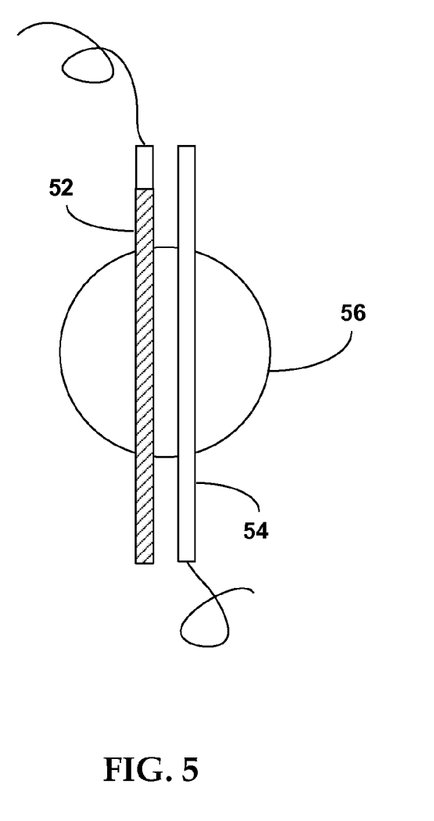
FIG. 5 is a top view of an exemplary experimental setup for testing electrodes.
Figure 5A:
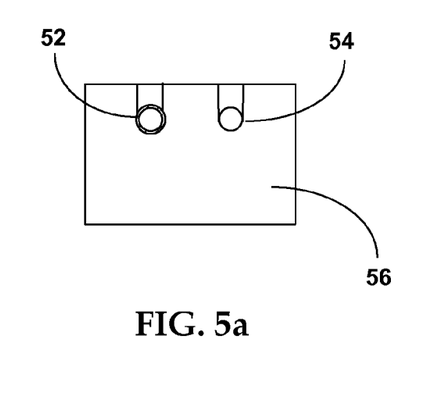
FIG. 5a is a cross-sectional view of FIG. 5 illustrating the electrodes positioned in two slots.

Various electrodes composed of a nickel alloy, Alloy 22, were evaluated using electrochemical impedance spectroscopy to measure the corrosion properties of an uncoated electrode, a DLC coated electrode and a DLC coated electrode that was immersed in a saturated acidic salt solution containing NaCl—$NaNO_3$—$KNO_3$ salt mixture at 150° C. for 1 week. FIGS. 5 and 5a illustrate the test set up, wherein a coated and uncoated electrode, 52 and 54 respectively, are suspended in a salt solution 56 of 0.01 M NaCl at 25° C.

Figure 6:
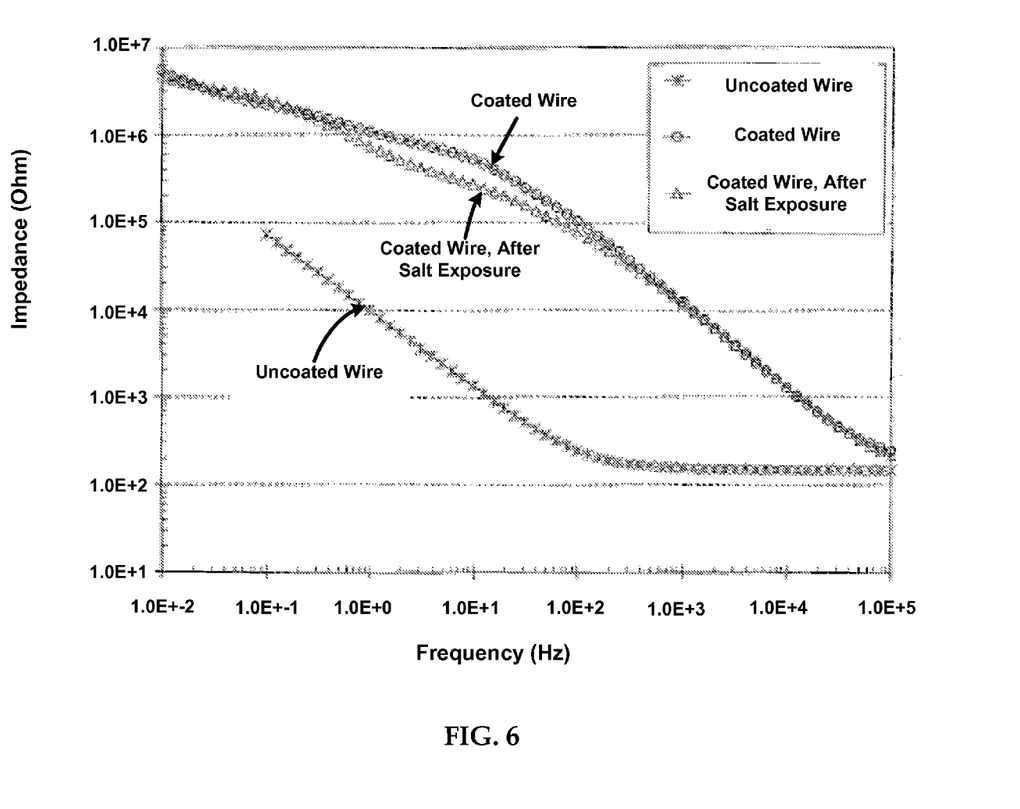
FIG. 6 is a plot of Impedance versus Frequency as measured by electrochemical impedance spectroscopy for coated and uncoated electrodes.

FIG. 6 illustrates that the impedance for the coated electrode, (designated as Coated Wire), was approximately about 1 megaohm at frequencies lower than 1 Hz and 1.5 to 2 orders of magnitude higher than that of the uncoated electrode (designated as Uncoated Wire). The impedance of the coated electrode immersed in the saturated acidic salt solution, (designated as Coated Wire, After Salt Exposure), was similar to that of the non-immersed coated electrode.

Example 2

A coupled multielectrode array sensor with nine DLC coated electrodes was fabricated. The electrode was flush mounted in the housing using epoxy such that the end surface of the electrode was exposed. A second coupled multielectrode array sensor with 16 uncoated electrodes flush-mounted in the same epoxy was also tested for comparison. Localized corrosion rates were measured using the uncoated sensor and the coated sensor in a saturated acidic NaCl—$NaNO_3$—$KNO_3$ salt mixture at 150° C. for one week.

Figure 7:
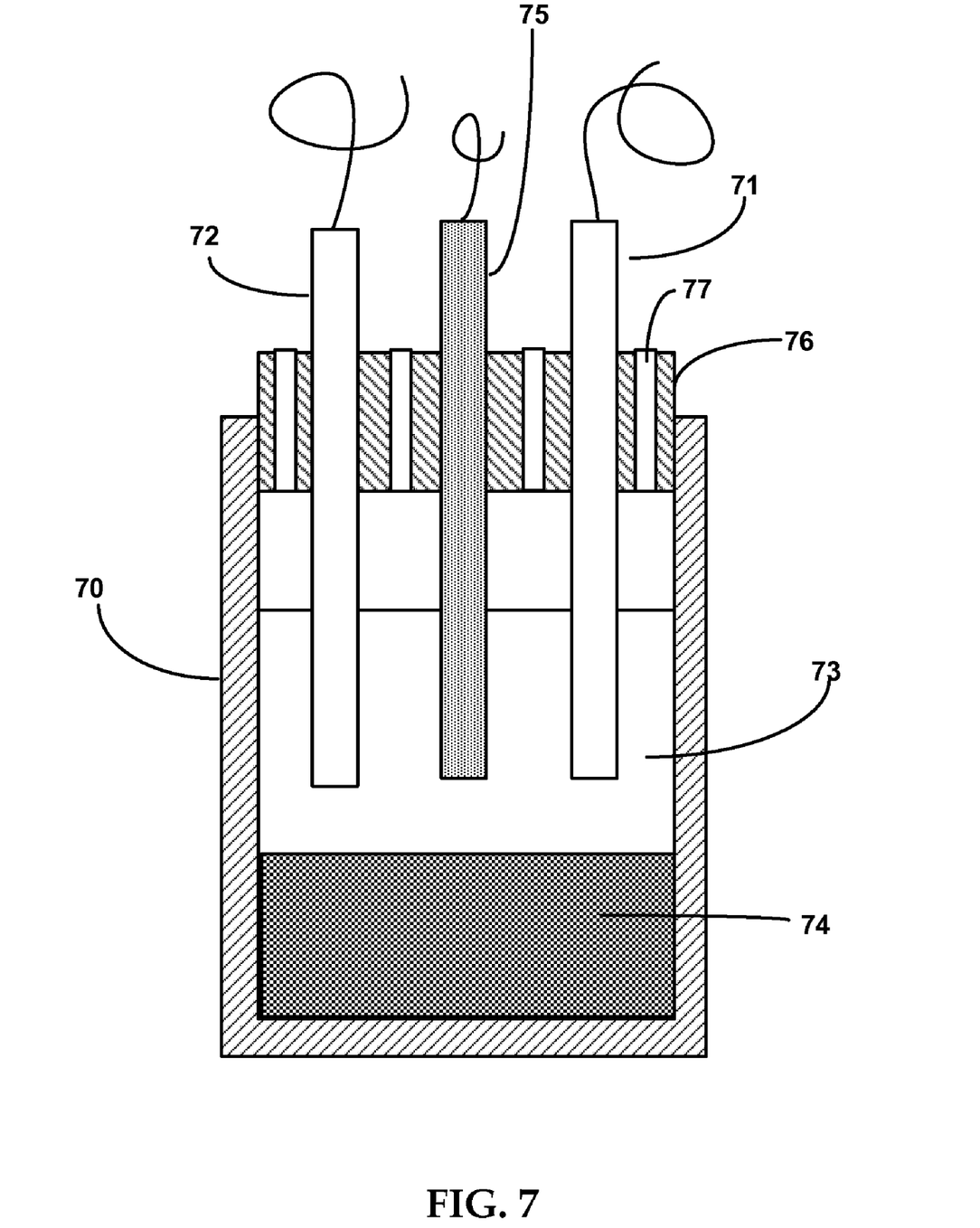
FIG. 7 is a cross-sectional view of an exemplary test setup for measuring the localized corrosion rate of the sensors discussed herein.

A schematic of the experimental set up is illustrated in FIG. 7, which shows a diagram of the vessel used in the immersion test. As can be seen from the figure, the sensors 71 and 72 were placed into a bath 70 of the salt solution 73, and solid salt mixture of the NaCl—NaNO$_3$—KNO$_3$ 74. A thermocouple 75 was also inserted into the bath 70 to measure the bath temperature. A cover 76 was placed on the bath to retain the sensors and thermocouple and provide venting of the bath through a number of vent holes 77.

Figure 8:
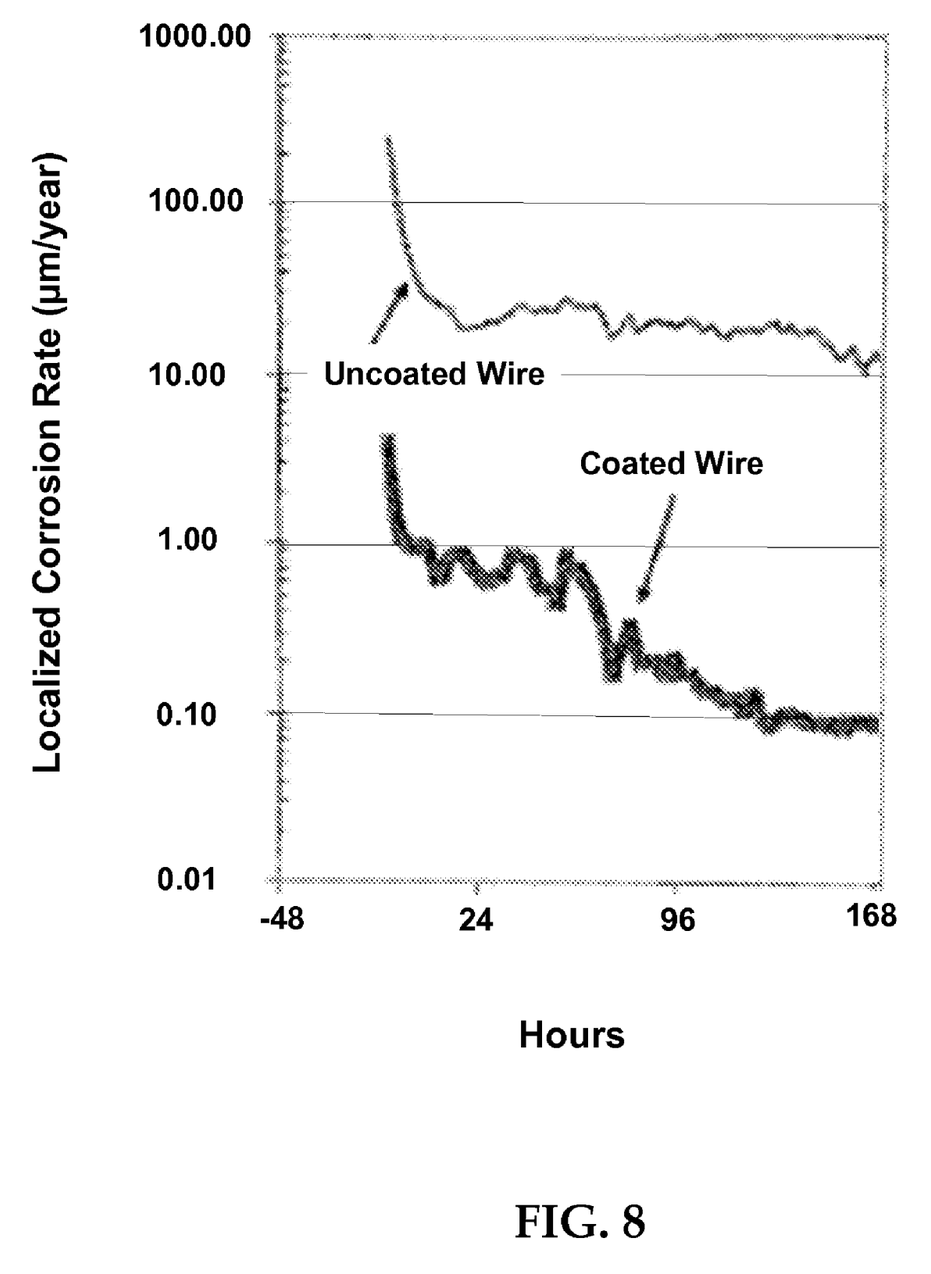
FIG. 8 is a plot of Localized Corrosion Rate versus Time for sensors containing coated and uncoated electrodes.

The results are illustrated in FIG. 8, which demonstrates that the sensor including the coated electrodes (Coated Wire) exhibited a localized corrosion rate of approximately 0.43 μm/year. Whereas the sensor with the uncoated electrodes (Uncoated Wire) exhibited a localized corrosion rate of approximately 10-40 μm/year, two orders of magnitude higher than the coated electrodes.

Upon inspection, the uncoated electrode was exposed to the salt solution at both the exposed end and side surfaces due to crevice formation between the electrode and the epoxy coating. The coated electrode was substantially free of crevice formation, i.e., less than 1.0 % of the surface area of the electrode sides, between the electrode and the epoxy coating.

The foregoing description is provided to illustrate and explain the present invention. However, the description hereinabove should not be considered to limit the scope of the invention set forth in the claims appended here to.

What is claimed is:

1. An electrochemical sensor capable of corrosion monitoring in a corrosive environment comprising:
a plurality of electrodes having longitudinal side surfaces and a tip including a diamond like carbon coating on said longitudinal surfaces of said electrodes having a thickness of equal to or greater than about 10 nanometers including an exposed surface area ($SA_1$) at said tip wherein said exposed surface area after exposure ($SA_2$) to a corrosive environment is defined as follows:

$$SA_2 \leq (1.05) \cdot (SA_1)$$

and said longitudinal side surfaces retain said diamond like carbon coating after exposure to a corrosive environment.

2. The sensor of claim 1 wherein said corrosive environment comprises an environment wherein said pH is greater than or lower than 7.0.

3. The sensor of claim 1 wherein said corrosive environment comprises 150° C. for 168 hours and a pH of less than 7.0.

4. The sensor of claim 3 wherein said corrosive environment includes an inorganic salt.

5. The sensor of claim 1 wherein one of said coated electrodes exhibits an impedance that is greater than one of said electrodes without said coating at frequencies of about $1 \times 10^0$ Hz to $1 \times 10^3$ Hz when immersed in a solution containing 0.1 M of NaCl at temperatures of at least about 25° C.

6. The sensor of claim 1, wherein said electrodes comprise a nickel alloy.

7. The sensor of claim 1, wherein said nickel alloy comprises nickel, chromium, molybdenum and tungsten.

8. The sensor of claim 1, wherein said coating further comprises a bond layer disposed between at least a portion of said electrode and said diamond like carbon coating.

9. The sensor of claim 8, wherein said bond layer comprises a silicon based compound.

10. The sensor of claim 1, wherein said sensor further comprising a housing surrounding at least a portion of each electrode, wherein said housing exhibits a service temperature of greater than or equal to about 50° C.

11. The sensor of claim 10, wherein said housing comprises a fluoropolymer material.

12. The sensor of claim 10, wherein said housing defines a plurality of openings therein and said electrodes are retained in said openings with a thermoset compound.

13. The sensor of claim 1 wherein said coating has a thickness of at least about 10 nm to about 50 microns.

14. A method of producing an electrochemical sensor capable of corrosion monitoring comprising:
depositing a diamond like carbon coating longitudinal side surfaces of an electrode including said longitudinal side surfaces and a tip, wherein said coating has a thickness of greater than 10 nanometers and said electrode tip has an exposed surface area ($SA_1$), wherein said exposed surface area after exposure ($SA_2$) to a corrosive environment is defined as follows:

$$SA_2 \leq (1.05) \cdot (SA_1),$$

and said longitudinal side surfaces retain said diamond like carbon coating after exposure to a corrosive environment.

15. The method of claim 14, wherein said electrode comprises a nickel alloy.

16. The method of claim 14, wherein said electrode comprises nickel, molybdenum, tungsten and chromium.

17. An electrochemical sensor capable of corrosion monitoring in a corrosive environment comprising:
a plurality of electrodes having longitudinal side surfaces and a tip including a diamond like carbon coating on said longitudinal surfaces of said electrodes having a thickness of greater than 1 micron including an exposed surface area ($SA_1$) at said tip and said longitudinal side surfaces retain said diamond like carbon coating after exposure to a corrosive environment;
said exposed surface area characterized as remaining substantially constant after exposure to a corrosive environment at a pH less than or greater than 7.0 for greater than 10 hours such that the exposed surface area after exposure ($SA_2$) to a corrosive environment is defined as follows:

$$SA_2 \leq (1.05) \cdot (SA_1).$$

18. The sensor of claim 17 wherein said corrosive environment comprises an environment wherein the temperature is greater than 25° C.

* * * * *